US006932817B2

(12) United States Patent
Baynham et al.

(10) Patent No.: US 6,932,817 B2
(45) Date of Patent: Aug. 23, 2005

(54) POLYAXIAL MODULAR SKELETAL HOOK

(75) Inventors: Bret O'Neil Baynham, Jupiter, FL (US); Matthew G. Baynham, Jupiter, FL (US)

(73) Assignee: Innovative Spinal Design, Riviera Beach, FL (US)

( * ) Notice: Subject to any disclaimer, the term of this patent is extended or adjusted under 35 U.S.C. 154(b) by 97 days.

(21) Appl. No.: 10/236,647

(22) Filed: Sep. 6, 2002

(65) Prior Publication Data

US 2003/0149435 A1 Aug. 7, 2003

Related U.S. Application Data

(60) Provisional application No. 60/353,215, filed on Feb. 1, 2002.

(51) Int. Cl.[7] .............................. A61B 17/70
(52) U.S. Cl. ......................... 606/61; 606/72
(58) Field of Search .............. 606/61, 60, 72, 606/73, 69, 70, 71, 76, 77, 78

(56) References Cited

U.S. PATENT DOCUMENTS 5,397,363 A    3/1995   Gelbard
5,584,832 A   12/1996   Schlapfer
5,688,273 A   11/1997   Errico et al.
5,752,957 A    5/1998   Ralph et al.
5,810,818 A    9/1998   Errico et al.
5,885,286 A    3/1999   Sherman et al.
6,352,537 B1 * 3/2002   Strnad ..................... 606/61

FOREIGN PATENT DOCUMENTS

EP            0 613 664 A2   12/1993

* cited by examiner

Primary Examiner—Cary E. O'Connor
Assistant Examiner—Candice C. Stokes
(74) Attorney, Agent, or Firm—McHale & Slavin, P.A.

(57) ABSTRACT

A modular skeletal hook has an upper module for connecting with larger support apparatus to maintain bones of the skeleton in fixed relationship. The upper module is connected to an attachment module by a modified ball and socket arrangement. The attachment module has a C-shaped hook for engaging the bone. The angular orientation of the upper module and the attachment module may be fixed by a set screw threaded through the upper module and the attachment module.

6 Claims, 1 Drawing Sheet

POLYAXIAL MODULAR SKELETAL HOOK

RELATED APPLICATIONS

This application is a continuation of Provisional Application No. 60/353,215 filed Feb. 1, 2002.

FIELD OF THE INVENTION

This invention relates to the field of orthopedic surgery. Particularly, the invention is directed to skeletal fixation apparatus and implants having adjustable angular orientation between the bone attachment element and the rods or plates connected thereto.

BACKGROUND OF THE INVENTION

The purpose of the implant is to reinforce certain parts of the skeleton by use of strategically placed bone attachment devices. In some cases, these devices may support alignment support rods placed bilateral along the vertebrae as well as cross-link plates that bridge the spine.

Conventionally, pedicle screws are use to attach the implants to the bone. However, there are instances in which it is not desirable or possible to use screws. Other attachment devices, such as hooks, may be used when it is not desirable to penetrate the bone. Usually, these hooks or screws are rigid one piece constructions. Due to the various anomalies of the skeleton, occurring naturally or by trauma, it is difficult to place a series of attachments in such a manner that a uniformly shaped plate or rod can be connected without creating additional stress on the skeleton.

Further, in the case of the hooks there is the possibility of movement of the attachment point.

DESCRIPTION OF THE PRIOR ART

U.S. Pat. No. 5,397,363 discloses a spinal stabilization implant system using pedicle screws. Also shown and described are hooks for attaching to the vertebrae. These screws and hooks are one piece devices without adjustment capabilities.

What is needed in the art is a bone attachment device that may be optimally attached to the bone, as dictated by the anatomy, with modular construction permitting changes in angular orientation of a portion of the device for connecting to support apparatus.

SUMMARY OF THE INVENTION

A modular skeletal hook is disclosed having an upper module for connecting to a larger support apparatus for maintaining bones of the skeleton in fixed relationship. The upper module is connected to an attachment module by a modified ball and socket arrangement. The attachment module has a C-shaped hook for engaging the bone. The angular orientation of the upper module and the attachment module may be fixed by a set screw threaded through the upper module and the attachment module.

Accordingly, it is an objective of the instant invention to teach a modular construction having a bone attachment portion and a polyaxial support portion.

It is a further objective of the instant invention to teach a bone hook formed with a ball socket with a threaded aperture through the socket.

It is yet another objective of the instant invention to teach a support module having a spherical area adapted to fit into the socket of the bone hook. The spherical area includes an aperture therethrough. Opposite the spherical area, the support module has a threaded connector for connecting to skeletal support devices.

It is a still further objective of the invention teach a set screw which has multiple functions of connecting the two major modules together, maintaining any angular orientation between the modules, and positively attaching the device to the bone.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Figure 1:
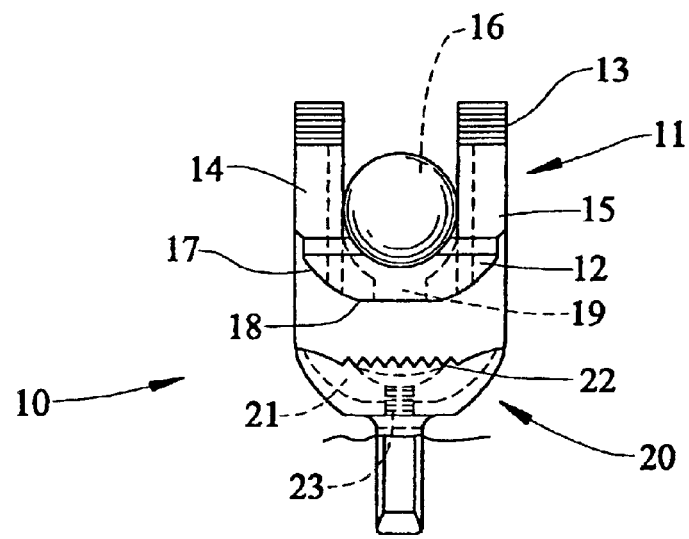
FIG. 1 is a side view of the polyaxial modular spinal hook of this invention.
Figure 3:
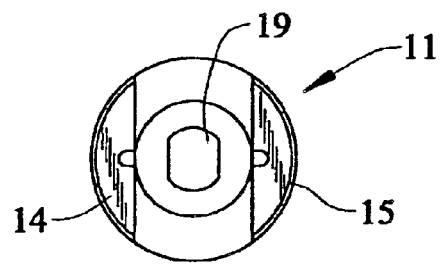
FIG. 3 is a top view of the support module showing the aperture.

The modular polyaxial bone fixation device 10, shown in FIG. 1, has an upper module 11 formed with a U-shaped connector 12. The connector 12 has external threads 13 about the upstanding legs 14 and 15 for accepting a threaded nut (not shown) to connect bone support apparatus between the legs. A cross section of a spinal rod 16 is shown in phantom lines. The bottom portion of the U-shaped connector 12 is shaped as a portion of a ball 17 or nearly spherical, shown in FIG. 3. As shown, there is a flattened area 18. The bottom portion 17 also has an aperture 19 therethrough.

Figure 2:
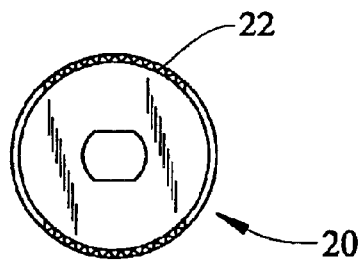
FIG. 2 is a top view of the ball socket module with aperture.

The attachment module 20 has a socket portion 21, shown in FIG. 2, shaped to accept the ball 17 of the connector module 11. The upper edge of the socket portion 21 has serrations 22 which act as stops for rotation when assembled. The socket portion has an aperture 23 extending through the thickened lower wall. The aperture has internal threads 27 to cooperate with the threads 28 of the set screw 26.

Figure 4:
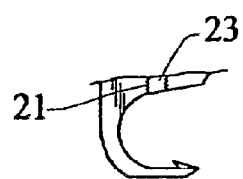
FIG. 4 is a side view of the attachment module.
Figure 5:
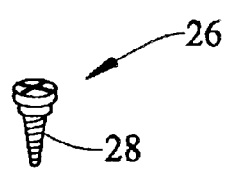
FIG. 5 is a perspective of the set screw.

Depending from the socket 21 is the C-shaped bone hook 25, shown in FIG. 4, which attaches to the skeletal bone of a patient. The exterior and interior walls of the hook 25 are flattened for greater purchase on the bone. Aperture 23 penetrates the portion of the bone hook joined to the socket 21. The set screw 26, shown in FIG. 5, is threaded through the upper module and the attachment module to movably connect the two elements.

In use, the skeletal bone is exposed and an attachment site is chosen. The hook 25 is attached to the bone. If a series of the devices is necessary, the several separate hooks are placed. The support modules of the several devices are then brought into alignment for placing support apparatus by manipulating the support module in the attachment module. Once this alignment is established each of the set screws in each of the modular sets are tightened to fix the angular orientation of the support module to accept another apparatus spanning the several modules. The threaded set screw also contacts the bone within the arc of the C-shaped hook to positively fix the device. The other support apparatus is then placed in the aligned U-shaped modules and the nut is threaded onto the U-shaped module to secure the apparatus.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

What is claimed is:

1. A modular polyaxial skeletal hook comprising a bone attachment module connected to an upper module through a polyaxial connection, a socket portion formed on said bone attachment module and said upper module having a nearly spherical portion, said socket portion and said nearly spherical portion cooperating forming a modified ball joint for universal adjustment of said bone attachment module and said upper module further comprising an upper edge on said socket portion, serrations on said upper edge for engaging said nearly spherical portion further comprising an aperture through said nearly spherical portion, a threaded set screw inserted in said aperture for fixing said upper module and said attachment module in a desired angular orientation further comprising a second aperture in said attachment module, said set screw traversing said second aperture and adapted to engage a skeletal bone further including screw threads in said second aperture cooperating with said threaded set screw.

2. A modular polyaxial skeletal hook comprising a bone attachment module connected to an upper module through a polyaxial connection, a socket portion formed on said bone attachment module and said upper module having a nearly spherical portion, said socket portion and said nearly spherical portion cooperating forming a modified ball joint for universal adjustment of said bone attachment module and said upper module, an aperture through said nearly spherical portion, a threaded set screw inserted in said aperture for fixing said upper module and said attachment module in a desired angular orientation, a second aperture in said bone attachment module, said set screw traversing said second aperture, screw threads in said second aperture cooperating with said threaded set screw.

3. A modular polyaxial skeletal hook of claim 2 further comprising an upper edge on said socket portion, serrations on said upper edge for engaging said nearly spherical portion.

4. A modular polyaxial skeletal hook of claim 3 further comprising said attachment module having a member for engaging the skeletal bone, said member in the formed in a generally C-shaped configuration.

5. A modular polyaxial skeletal hook of claim 3 further comprising said upper module formed in a U-shaped configuration with a nearly spherical portion connecting upstanding legs, said legs adapted to seat a bone support apparatus between said legs, said legs having interrupted screw threads about the free ends, said screw threads adapted to cooperate with a threaded nut.

6. A modular skeletal hook of claim 5 further comprising said nearly spherical portion including a flattened area in contact with said socket.

* * * * *